(12) United States Patent
Bandyopadhyay et al.

(10) Patent No.: US 9,175,281 B2
(45) Date of Patent: Nov. 3, 2015

(54) PROCESS FOR THE PURIFICATION OF TISSUE PLASMINOGEN ACTIVATOR

(75) Inventors: Sanjay Bandyopadhyay, Gujarat (IN); Sanjeev Kumar Mendiratta, Gujarat (IN); Sushobhan Bandyopadhyay, Gujarat (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 191 days.

(21) Appl. No.: 13/885,002

(22) PCT Filed: Nov. 15, 2011

(86) PCT No.: PCT/IN2011/000790
§ 371 (c)(1), (2), (4) Date: Jun. 20, 2013

(87) PCT Pub. No.: WO2012/066569
PCT Pub. Date: May 24, 2012

(65) Prior Publication Data
US 2013/0330808 A1    Dec. 12, 2013

(30) Foreign Application Priority Data
Nov. 16, 2010   (IN) .......................... 3127/MUM/2010

(51) Int. Cl.
*C12N 9/72*    (2006.01)
(52) U.S. Cl.
CPC ....... *C12N 9/6459* (2013.01); *C12Y 304/21069* (2013.01)

(58) Field of Classification Search
None
See application file for complete search history.

(56) References Cited

U.S. PATENT DOCUMENTS 5,094,960 A * 3/1992 Bonomo ...................... 436/178
5,141,862 A * 8/1992 Patel et al. ................... 435/226
5,641,655 A * 6/1997 Foster et al. ................. 435/69.7

OTHER PUBLICATIONS

Kvassman et al. (Fibrinolysis, 1995, vol. 9, pp. 215-221).*
Queiroz et al. (Journal of Biotech., vol. 87, 2001, pp. 143-159).*
Burck, P.J., et al. "Characterization of a modified human tissue plasminogen activator comprising a Kringle-2 and a protease domain", The Journal of Biological Chemistry, vol. 265, No. 9, Mar. 25, 1990, pp. 5170-5177, XP001317617.
Denman J. et al., "Transgenic expression of a variant of human tissue-type plasminogen activator in goat milk; purification and characterization of the recombinant enzyme," Bio/Technology, Nature Publishing Co. New York, US, vol. 9, Oct. 1, 1991, p. 839, XP000749774, ISSN 0733-222X, DOI: 10.1038/NBT0991-839.

* cited by examiner

*Primary Examiner* — Hope Robinson
(74) *Attorney, Agent, or Firm* — McCarter & English, LLP; Steven G. Davis; Wei Song (57) ABSTRACT

The present invention provides process of purification of tissue plasminogen activator (tPA) from a crude mixture or a partially purified mixture containing tPA protein and impurities by using hydrophobic interaction column chromatography, optionally in combination with ion exchange column chromatography.

25 Claims, 5 Drawing Sheets

Figure 1

IPA – isopropyl alcohol

PROCESS FOR THE PURIFICATION OF TISSUE PLASMINOGEN ACTIVATOR

RELATED APPLICATIONS

This application is a 35 U.S.C. §371 national stage filing of International Application No. PCT/IN2011/000790, filed Nov. 15, 2011, which claims priority under 35 U.S.C. §365 to India Patent Application Serial No. 3127/MUM/2010, filed Nov. 16, 2010. The entire contents of each of the aforementioned applications are incorporated herein by reference in their entirety.

The present invention relates to a process of purification of tissue plasminogen activator protein (tPA) from a mixture comprising the said protein and other impurities. Specifically, the present invention describes the purification of tPA in its desired form which mainly comprises of the single-chain form of the said protein by using a hydrophobic interaction chromatography in the presence of a suitable solvent.

BACKGROUND OF THE INVENTION

Plasminogen activators are serine proteases that convert the catalytically inactive zymogen plasminogen to its active form, plasmin, which is required for the dissolution of fibrin. Because of this property, several plasminogen activators are now being used as in-vivo fibrinolytic agents in the treatment of acute myocardial infarction. One such plasminogen activator is tissue plasminogen activator, which has been the focus of considerable attention because of its enhanced fibrinolytic activity in the treatment of acute myocardial infarction and pulmonary embolism.

Human tissue plasminogen activator, a serine protease containing 527 amino acids with 17-pairs of S—S cross-links is a single polypeptide chain glycoprotein with a molecular mass of about 70 kDa. The glycosylated tPA is found to appear with two different forms—Type I and Type II. The carbohydrate moiety mainly comprises of N-linked and O-linked glycosylations at the positions $Asn^{448}$, $Asn^{117}$ and $Asn^{184}$ (N-linked) and $Thr^{61}$ (O-linked) glycosylation and contributes about 7% of the total molecular weight of the protein. Type I tPA is known to contain glycosylated moiety on all the above specified residues, whereas Type II population of tPA does not exhibit glycosylation at the position $Asn^{184}$ (Kazuya Mori Jr Biol. Chem. 1995 Feb. 17; 270(7): 3261-7). The isolated human tPA exhibits an isoelectric pH of about 7.5. Although tPA is synthesized inside the cell as a single-chain polypeptide, it has been reported that upon releasing in to the extracellular medium tPA gets proteolytically cleaved by plasmin at the C-terminus of $Arg^{275}$ (Kazuya Mori J Biol. Chem. 1995 Feb. 17; 270(7):3261-7). Proteolytic cleavage converts the single chain tPA in to a two-chain form which remains held together by a single S—S bond. However, it is known in the art that the single- and double-chain forms of tPA do not show any significant difference in fibrinolytic activity.

TNKase (TNK-tPA), a recombinant form human tPA is produced in CHO cells as a secretary protein and is known to play the same role as human tPA. Recombinant tPA is used as a therapeutic agent for the treatment of acute myocardial infarction. TNK-tPA has three sets of mutations on its polypeptide backbone at the positions $T^{103}N,N^{117}Q$, $KHRR^{(296-299)}AAAA$, as demonstrated in (Proc. Natl. Acad. Sci. Vol. 91, pp. 3670-3674, April 1994) and also in U.S. Pat. No. 5,612,029. Similar to that of the human tPA, the recombinant TNK-tPA also consists of Type I and Type II glycoforms and has been observed to appear as a mixture of single- and double-chain form.

It has been reported that single chain species of recombinant tPA (produced by CHO) with more than 70% purity of the single-chain form remains stable for more than 2.5 y when stored in lyophilized form, under room temperature conditions (Journal of Interventional cardiology, Vol 2, No 2, 1989). It has been also demonstrated that the double chain species of recombinant tPA (cleaved form) obtained from CHO cells remains fairly stable in liquid formulation for at least 1 year, when stored between 0-4° C. These observations indicate that both the single-chain and double-chain forms of tPA remain reasonably stable under various storage conditions.

For commercial purpose, recombinant tissue plasminogen activator or TNK-TPA has been overexpressed in CHO cells and purified with the help of various column chromatography steps. These chromatography steps mostly comprise of certain affinity column chromatography matrices to isolate tPA with its species variants like Type I and Type II in a selective manner. One such widely used affinity chromatography is Lysine-sepharose column chromatography. Lysine-sepharose matrix binds to tPA by the lysine-binding site of its kringle 2 domain. Therefore, this column step has been found to be useful in capturing the tPA molecule in a selective manner from crude mixture during column purification (Byeon I J, Kelley R F, Llinas M. Eur J. Biochem. 1991 Apr. 10; 197(1):1155-65). Further, U.S. Pat. No. 4,898,825 disclose the use of Erythrina trypsin inhibitor as an affinity agent for the purification of tPA. U.S. Pat. No. 5,411,864 discloses the use of antibodies for the purification of tPA. Similarly, U.S. Pat. No. 5,015,583 discloses the use of heparin sepharose affinity column for the purification of tPA. U.S. Pat. No. 5,141,863 disclose the use of hydroxyapatite column for the purification of tPA.

Hence, a wide variety of chromatography processes, e.g. affinity and hydroxyapatite, have been applied for the purification of tPA. However, the cost of affinity or hydroxyapatite matrices is very high and therefore, not very cost effective for industrial use. Besides, none of the process has been reported yet to give rise to a desired mixture of the single- and double-chain forms of tPA while removing the excess amount of double chain form of the said protein during purification. In the absence a suitable process, the process of tPA purification remains a challenge. Hence, there is a need to develop an industrially viable, cost effective process for the purification of the desired tPA preparation.

Thus, the present invention solves the problem associated with the process described in the prior art and also brings scientific advancement which makes the present process advantageous over the processes known in the prior art related to the purification of tPA in its desired form. In the present purification process, tPA is captured first from a crude mixture without any significant loss of the desired protein and is eluted in a differential manner from a hydrophobic column in the presence of a suitable organic solvent while removing the undesired contaminating proteins and species variants.

OBJECTIVES OF THE INVENTION

A process for the purification of tissue plasminogen activator comprises
a) loading the mixture of tissue plasminogen activator with impurities on to a suitable column matrix
b) eluting the impurities from the said column matrix with a suitable solvent at appropriate concentration.

c) eluting the desired form of the said protein from the said column matrix with a suitable organic solvent at appropriate concentration.
d) obtaining the said protein in its desired form
e) optionally, an ion exchange column step is used before or after using the said suitable column matrix.

In embodiment the present invention provides the use of hydrophobic interaction column chromatography to purify the plasminogen activator in its desired form.

In another embodiment the present invention provides a process for the purification of tissue plasminogen activator comprises
a) loading the mixture of tissue plasminogen activator with other impurities on to a hydrophobic interaction column matrix.
b) eluting the impurities from the said column matrix with a suitable solvent at appropriate concentration
c) eluting the desired form of the said protein from the hydrophobic column matrix with a suitable organic solvent at appropriate concentration.
d) obtaining the tissue plasminogen activator in the desired form
e) optionally, an ion exchange column step is used before or after using the hydrophobic column step.

In yet another embodiment, the invention provides purified tissue plasminogen activator comprises a suitable mixture of single chain and double chain.

In embodiment the invention provides a mixture of desired form of tPA, which predominantly comprises the single-chain form of tissue plasminogen activator.

In yet another embodiment, the invention provides the desired form of tissue plasminogen activator preparation containing at least 55% single-chain form of tPA.

In another embodiment the invention provides a preparation of tPA, which predominantly comprises of the double-chain form of tissue plasminogen activator.

In an embodiment the invention provides the use of an organic solvent, isopropyl alcohol in the range of about 5% to 30% for purification of tissue plasminogen activator in its desired form.

In embodiment the invention provides a process for the purification of tissue plasminogen activator comprises
a) loading the mixture of tissue plasminogen activator with other impurities on to a hydrophobic interaction column matrix
b) washing of the hydrophobic interaction column matrix with less than 15% IPA to remove the impurities
c) eluting the tissue plasminogen activator in its desired form by 15% to 30% of isopropyl alcohol through the hydrophobic column matrix, which comprises predominantly the single-chain form of tPA with some amount of the double-chain form of the said protein
d) optionally, eluted tissue plasminogen activator in its desired form is further subjected to an ion exchange column chromatography.

The process for the purification of tissue plasminogen activator comprises
a) loading the mixture of tissue plasminogen activator with impurities on to a hydrophobic interaction column matrix.
b) eluting the tissue plasminogen activator by isopropyl alcohol in the concentration range of more than 18% from the hydrophobic interaction column matrix.
c) eluted tissue plasminogen activator is further subjected to at least one suitable matrix to elute the tissue plasminogen activator in its desired form.

SUMMARY OF INVENTION

The present invention provides a process of purification of tissue plasminogen activator (tPA) in its desired form from a crude mixture of proteins or partially purified mixture containing tPA protein with other impurities by using a hydrophobic interaction column chromatography, optionally in combination with ion exchange column chromatography. In the process of purification, tPA protein in its desired form is purified from a crude mixture or partially purified mixture mainly by using a hydrophobic column while removing the impurities from the desired form of tissue plasminogen activator. In an embodiment the purified tPA molecule in its desired form obtained from the said column after elution predominantly comprises of the single-chain (intact) variant of the said protein. In embodiment the desired form of tPA comprises 55% to 80% of single chain form of tPA. In preferred embodiment the desired form of tPA comprises 60% of single chain form of tPA. Moreover, the present invention also provides a process by which the single-chain variant or the double-chain variant of tPA molecule can be isolated in two different fractions from a crude mixture by differential elution of the protein in the presence of varying concentrations of a suitable organic solvent through a hydrophobic interaction column. Optionally, an ion exchange column chromatography is used in the process of purification of the said protein molecule to remove the undesired contaminants.

BRIEF DESCRIPTION OF FIGURES

Lane 1—Crude harvest; Lane 2—Flow-through and wash fraction; Lane 3—Predominantly double-chain form eluted with 12.5% isopropyl alcohol; Lane 4—Desired form of tPA eluted with 20% isopropyl alcohol.

DETAILED DESCRIPTION OF INVENTION

As used herein, the term "tissue plasminogen activator" refers to the human extrinsic (tissue-type) plasminogen activator having fribrinolytic activity that typically has a structure with five domains (finger, growth factor, kringle-1, kringle-2, and protease domains), but nonetheless it may have fewer domains or may have some of its domains repeated and act as a thrombolytic agent and retains the N-linked glycosylation sites at positions 117, 184, and 448. At minimum, the tissue plasminogen activator consists of a protease domain that is capable of converting plasminogen to plasmin, and an N-terminal region believed to be at least partially responsible for fibrin binding positions corresponding to amino acid positions 117, 184, and 448 of the wild type human tissue plasminogen activator. The retention of these glycosylation sites is due to the fact that variable site occupancy of recombinant and melanoma-derived wild-type tissue plasminogen activator leads to production of two variants, designated as Type I tissue plasminogen activator and Type II tissue plasminogen activator, respectively. Type I tissue plasminogen activator contains N-linked oligosaccharides at position 117, 184, and 448. Type II tissue plasminogen activator contains N-linked oligosaccharides at position 117, and 448. It is also understood that natural allelic variations exists and can occur among individuals, as demonstrated by one or more amino acid differences in the amino acid sequence of tissue plasminogen activator of each individual.

The term "tPA" used herein, refers to "tissue plasminogen activator", which includes human tissue plasminogen activator or its mutants or its variants based on the glycosylation pattern (type I and type II), either produced by cells endogenously or by recombinant DNA technology.

"Double-chain (Chain A and Chain B) or cleaved chain form of tPA" refers to human tissue plasminogen activator or its mutants or its variants, which is formed by autocatalytic or proteolytic cleavage of the said protein between $Arg^{275}$ and $Ile^{276}$ resulting in the formation of two chains separated on the basis of their apparent molecular weight by reducing SDS-PAGE and named, Chain A (slow moving form) and Chain B (fast moving form). Chain A and Chain B remain held together by one pair of S—S cross-link, under native conditions:

On the other hand, "single-chain or intact form of tPA" refers to a single chain form of human tissue plasminogen activator or its mutants or its variants, which does not show any cleavage on its polypeptide chain backbone.

The term "TNK-tPA", used herein refers to "tissue plasminogen activator", which includes human tissue plasminogen activator or its mutants or its variants based on mutations at $T^{103}N, N^{117}Q, KHRR^{(296-299)}AAAA$ either produced by cells endogenously or produced by using recombinant DNA technology. Moreover the suitable TNK-tPA comprises the appropriate ratio of single- and double-chain species. An example of tPA includes TNKase or TNK-tPA which are well known in the art. Hereinafter TNKase or TNK-tPA a genetically engineered form of wild type tPA is considered as species of tPA.

The term "desired form of tPA" used hereinafter describes a preparation of IPA, which mainly comprises of the single-chain form with some amount of the double-chain form of tPA protein.

The term "Chinese Hamster Ovarian cells" (CHO cells) are the cells originally obtained from Chinese Hamster ovaries. These are transfected with the gene of interest so that the protein of interest can be expressed under experimentally suitable conditions.

The term 'impurities' used herein refers to the contaminating and/or product-related proteins that are obtained along with the protein of interest from the host cell.

The term "crude mixture" refers to the supernatant which is obtained from the CHO cell culture by conventional adherent or suspension or perfusion fermentation process where the protein is secreted in the extracellular medium and can be obtained from the supernatant.

The term "partially purified mixture" of tPA protein refers to mixture containing tPA protein with product-related and process-related impurities which is obtained by any purification process known in the art.

The present invention provides a process for the purification of plasminogen activator or their species by using suitable purification matrix in the presence of suitable concentration of organic solvents.

In an embodiment, the present invention provides a process for the purification of plasminogen activator (tPA) comprises
a) Loading the mixture of tissue plasminogen activator with impurities on to a suitable column matrix
b) Eluting the impurities from the said column matrix with a suitable solvent at appropriate concentration.
c) Eluting the desired form of the said protein from the said column matrix with a suitable organic solvent at appropriate concentration.
d) Obtaining the said protein in its desired form
e) Optionally, an ion exchange column step is used before or after using the said suitable column matrix.

In such embodiment the suitable purifying matrix is hydrophobic interaction chromatography. The hydrophobic interaction column matrix used in the present invention includes but is not limited to butyl sepharose 6 FF, Phenyl sepharose 6 Fast Flow, Octyl sepharose 4 Fast Flow. The plasminogen activator is plasminogen activator (tPA) or TNK-tPA or r-tPA or r-PA or n-PA, preferably TNK-tPA. The suitable solvent is selected from ethanol, methanol, isopropyl alcohol (IPA), preferably isopropyl alcohol. Appropriate oncentration of isopropyl alcohol is important to isolate the desired form of tPA from hydrophobic interaction column while removing the impurities. In an embodiment, about 5% to about 30% of isopropyl alcohol is used to purify the tPA protein in a differential manner through the hydrophobic column. In a preferred embodiment, about 5% to about 15% isopropyl alcohol is used to remove the impurities comprising double chain form of tPA from the said column matrix and about 15% to about 30% isopropyl alcohol is used to elute the desired form of tPA from the column. In a more preferred embodiment, substantial removal of impurities comprising double chain form is carried out with 10% to 12.5% of isopropyl alcohol and elution of the desired form of tPA is performed with 18% to 20% isopropyl alcohol. In most preferred embodiment, removal of impurities is carried out with 12.5% isopropyl alcohol and elution of the desired form of tPA protein is conducted with 20% isopropyl alcohol. The desired form of eluted tPA mainly comprises of the single-chain form of tPA. In embodiment the desired form of tPA comprises 55% to 80% single chain form of tPA. In preferred embodiment the desired form of tPA comprises 60% single chain form of tPA. The said process does not involve any affinity chromatography step for purification of the desired form of tPA.

In one of the preferred embodiment, the invention provides a process for the purification of tissue plasminogen activator comprises
a) Loading the mixture of tissue plasminogen activator with other impurities on to a hydrophobic interaction column matrix
b) Washing of the hydrophobic interaction column matrix with less than 15% IPA to remove the impurities
c) Eluting the tissue plasminogen activator in its desired form by 15-30% of isopropyl alcohol through the hydrophobic column matrix, which comprises predominantly the single-chain form of tPA with some amount of the double-chain form of the said protein
d) Optionally, eluted tissue plasminogen activator in its desired form is further subjected to an ion exchange column chromatography.

In such embodiment, concentration of isopropyl alcohol used in step (b) is about 5% and in a preferred embodiment concentration of isopropyl alcohol used in step (b) is about 10%. In most preferred embodiment, concentration of isopropyl alcohol used in step (b) is about 12.5%. The impurity which is removed in step (b) comprises double chain of tPA and process related impurity. In step (b) impurity is completely or substantially removed in the presence of isopropyl alcohol.

In such embodiment, concentration of isopropyl alcohol used in step (c) is about 18% and in preferred embodiment, concentration of isopropyl alcohol used in step (c) is about 20%. The present invention also optionally provides the use of a cation exchange column chromatography for further removal of impurities from the desired form of tPA.

In embodiment the desired form of tPA, mentioned in step (c) comprises 55% to 80% single chain form of tPA. In preferred embodiment the desired form of tPA comprises 60% single chain form of tPA.

In another embodiment, the invention process for the purification of the desired form of tissue plasminogen activator comprises
a) loading the mixture of tissue plasminogen activator with impurities on to a hydrophobic interaction column matrix.
b) eluting the tissue plasminogen activator by isopropyl alcohol in the concentration range of more than 18% from the hydrophobic interaction column matrix.
c) eluted tissue plasminogen activator is further subjected to at least one suitable matrix to elute the tissue plasminogen activator in its desired form.

In such embodiment, concentration of isopropyl alcohol used in step (b) is about 18% to 40% and in a preferred embodiment concentration of isopropyl alcohol used in step (b) is about 18%. In most preferred embodiment concentration of isopropyl alcohol used in step (b) is about 20%. The suitable matrix is selected from ion exchange, hydroxyapatite, affinity chromatography and hydrophobic interaction chromatography.

In the present invention, crude preparation of tPA is obtained from genetically engineered CHO cells harboring the gene that encodes the said protein, as a secretory protein in the cultured supernatant. This crude preparation is first subjected to hydrophobic interaction column chromatography for purification in capture-elution mode. Optionally, an ion exchange column may be used after the hydrophobic interaction column step for the removal of other impurities present in the crude mixture. In preferred embodiment, the hydrophobic interaction column is used first as the first step of purification in capture-elution mode.

Alternatively, tPA is obtained from genetically engineered CHO cells as a secretory protein in the cultured supernatant which is partially purified by purification process known in the art and thereafter it is further purified by using a hydrophobic interaction column chromatography step, wherein the said protein is purified in its desired form by using the said column in capture-elution mode. Optionally, ion exchange chromatography can be used after the hydrophobic interaction column step for further purification. In preferred embodiment, the hydrophobic interaction column is used first, as the capturing step for the purification of tPA from a semi-purified preparation, optionally, after which an ion exchange chromatography can be used for the removal of other impurities. The said ion exchange column is used in bind-elute mode, wherein elution from the column is carried out in the presence of high salt concentration e.g. NaCl or KCl or $Na_2SO_4$ or $(NH_4)_2SO_4$ are used with a suitable buffer. Ion exchange column used according to the present invention is a cation exchange column. Preferably strong cation exchange column is used which include but is not limited to SP sepharose, SP-5PW etc.

The present invention is advantageous over the known processes of purification of tPA as it provides direct capturing of the tPA protein by the hydrophobic column matrix from a crude mixture or partially purified preparation of tPA without any significant loss of the desired protein without using any affinity column chromatography. In addition, the present process also makes it possible to isolate the desired form of tPA while removing the other impurities in a selective manner. The desired form of isolated tPA preparation mainly comprises of the single-chain form of tPA. Therefore, the present invention provides a high yielding, robust and a cost effective purification process of tPA protein.

The present invention further provides a pharmaceutical composition of tissue plasminogen activator where tPA is purified in its desired form mainly comprising of the single-chain form of the said protein by using a hydrophobic interaction column matrix in the presence of an organic solvent.

Pharmaceutical composition comprises tissue plasminogen activator, which is obtained by the purification process described in the present invention and a pharmaceutically acceptable diluent or carrier. The composition of present invention can be formulated in lybphilized form.

The invention is explained in greater detail by the examples demonstrated below, which are provided by way of illustration only and therefore should not be construed to limit the scope of the invention.

EXAMPLE 1

Figure 1:
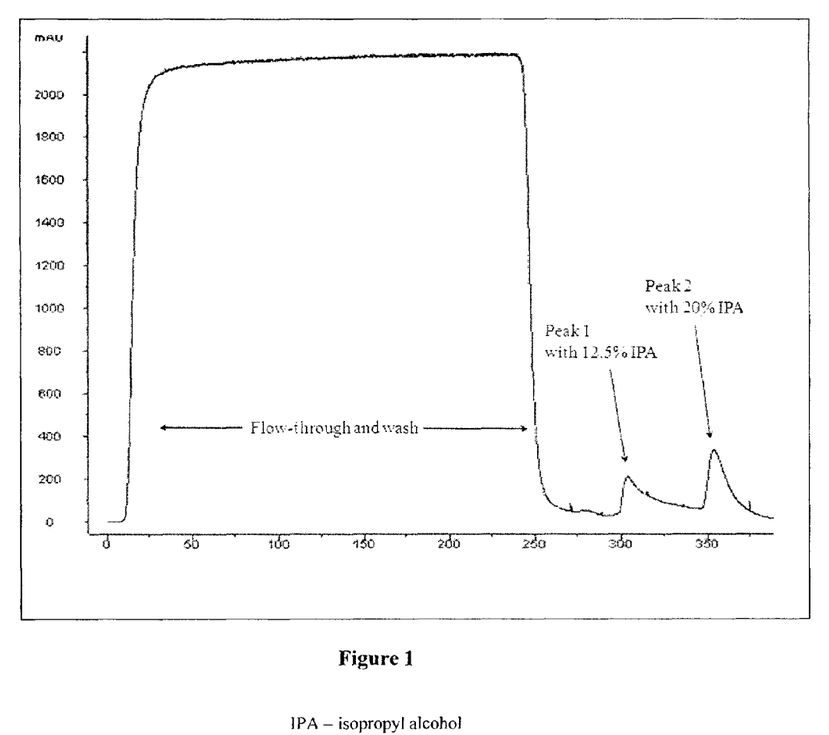
FIG. 1 illustrates a chromatogram of TNK-tPA purification from crude harvest by hydrophobic interaction column chromatography. Peak 1—with 12.5% isopropyl alcohol; Peak 2—with 20% isopropyl alcohol.
Figure 2:
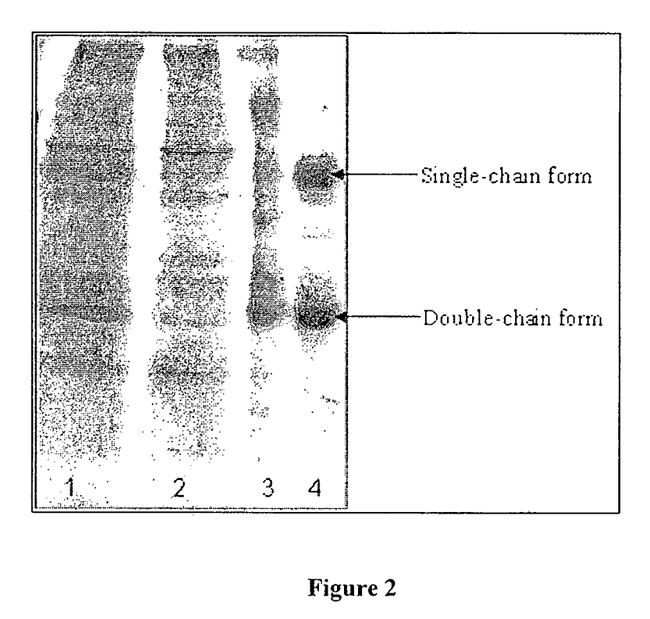
FIG. 2 illustrates polypeptide profile of column-eluted TNK-tPA by reducing SDS-PAGE after purifying by hydrophobic interaction column chromatography step.

The gene of tPA was modified to incorporate the desired mutations, $T^{103}$ N, $N^{117}$Q, KHRR$^{(296-299)}$AAAA, to produce TNK-tPA, as reported in (PNAS, 1994, vol 91, 3670-3674). This modified gene was cloned in a vector derived from pZRC (WO 2007/017903) and the final expression vector containing the TNK-tPA gene was used to produce stable transfectants of CHO K1 cells. Production of TNK-tPA from stably transfected CHO K1 cells was performed as follows. The growth and production was carried out in the batch or fed-batch mode by using a commercially available serum free and chemically defined media. Further in the fed-batch process, the fed-batch feeding was done by using a concentrated feed of the same media starting from the $3^{rd}$ day of growth and at regular intervals up to the $10^{th}$ day of the process. The cells were cultured at 37° C. in a humidified 5% $CO_2$ environment under shaking conditions with the agitation speeds ranging from 50 RPM to 200 RPM using the spinner flasks. The cells were grown up to cell densities ranging from 3.0-4.0 million cells/mL and cell viability was maintained >75% to obtain optimal expression of the desired protein. The process was continued, under the conditions mentioned above for a period ranging from 8 to 11 days. The cultured supernatant containing the TNK-tPA protein was loaded, on to a butyl sepharose 6 Fast Flow column. The column was equilibrated with 20 mM Tris-Cl buffer of pH 7.0 containing 750 mM NaCl. After loading, the column was washed with 12.5% isopropyl alcohol in equilibration buffer. The desired form of tPA was eluted with the 20% isopropyl alcohol in the same buffer, as shown in FIG. 1 and FIG. 2. In 12.5% isopropyl alcohol column-fraction, majorly the double-chain form of TNK-tPA and contaminating impurities were observed to come out of the column, whereas the desired form of TNK-tPA, which mainly comprises of the single-chain form of TNK-tPA was found to elute out in 20% isopropyl alcohol fraction.

EXAMPLE 2

The cultured supernatant containing TNK-tPA protein, as described in example 1, was loaded on to a butyl sepharose 6

Figure 3:
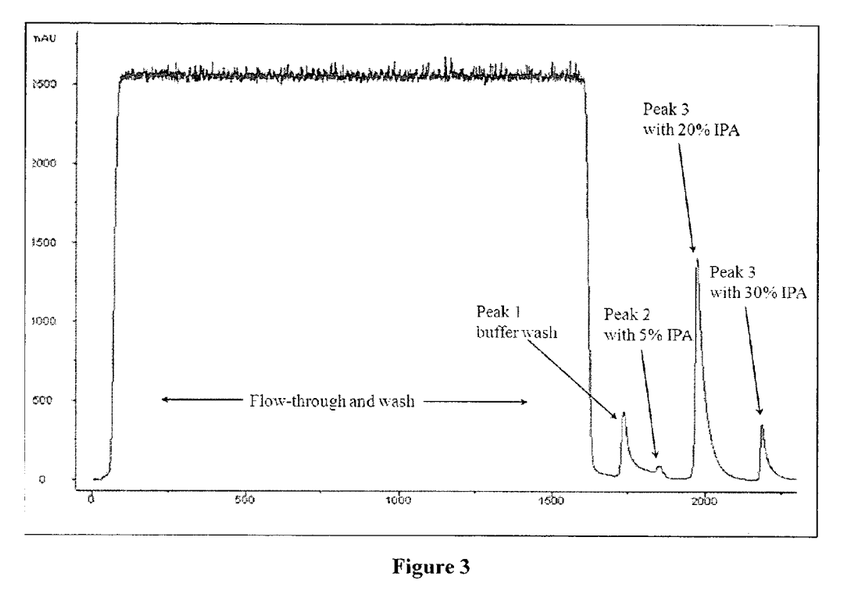
FIG. 3 illustrates a chromatogram of TNK-tPA purification from crude harvest by hydrophobic interaction column chromatography—Peak 1—buffer-wash (no NaCl); Peak 2—with 5% isopropyl alcohol; Peak 3—with 10% isopropyl alcohol; Peak 3—with 20% isopropyl alcohol; Peak 4—with 30% isopropyl alcohol.

Fast Flow column. The column was equilibrated with 20 mM Tris-Cl buffer of pH 7.0 containing 750 mM NaCl. After loading, the column was washed with the equilibration buffer devoid of NaCl followed by a second wash with buffer containing 5% isopropyl alcohol. The desired protein was eluted out with buffer containing 20% isopropyl alcohol. The column was further washed with buffer containing 30% isopropyl alcohol to recover the strongly bound tPA protein. Fraction eluted with 20% isopropyl alcohol was found to contain the desired form of tPA protein mainly comprising of the single-chain form of TNK-tPA, as shown in FIG. 3.

EXAMPLE 3

Figure 4:
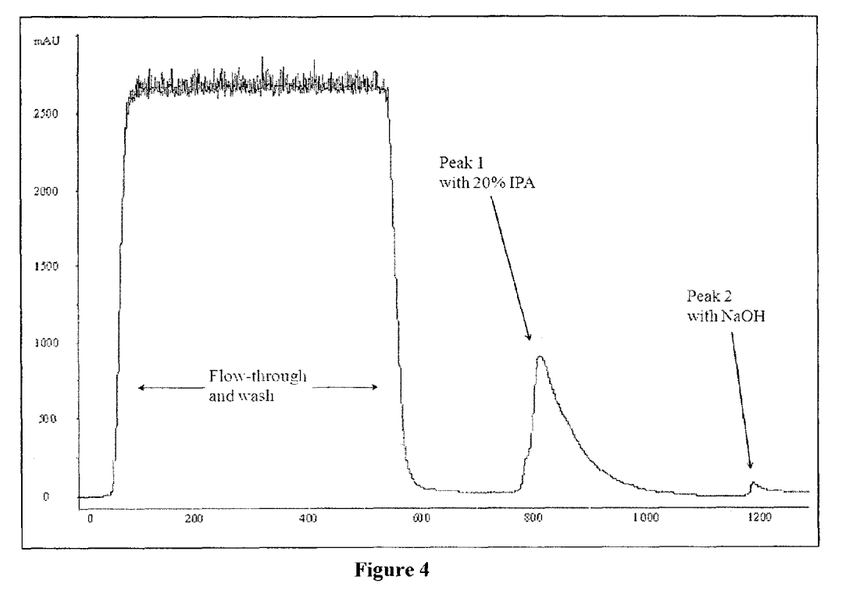
FIG. 4 illustrates a chromatogram of TNK-tPA purification from crude harvest by hydrophobic interaction column chromatography. Peak 1—with 20% isopropyl alcohol; Peak 2—NaOH wash.

The cultured supernatant containing TNK-tPA protein, as described in example 1, was loaded on to a butyl sepharose 6 FF column. The column was equilibrated with 20 mM Tris-Cl buffer of pH 7.0 containing 750 mM NaCl. After loading, the column matrix-bound protein was eluted with the same equilibration buffer containing 20% isopropyl alcohol. Majority of the tPA protein was found to elute out of the column with 20% isopropyl alcohol as shown in FIG. 4.

EXAMPLE 4

Figure 5:
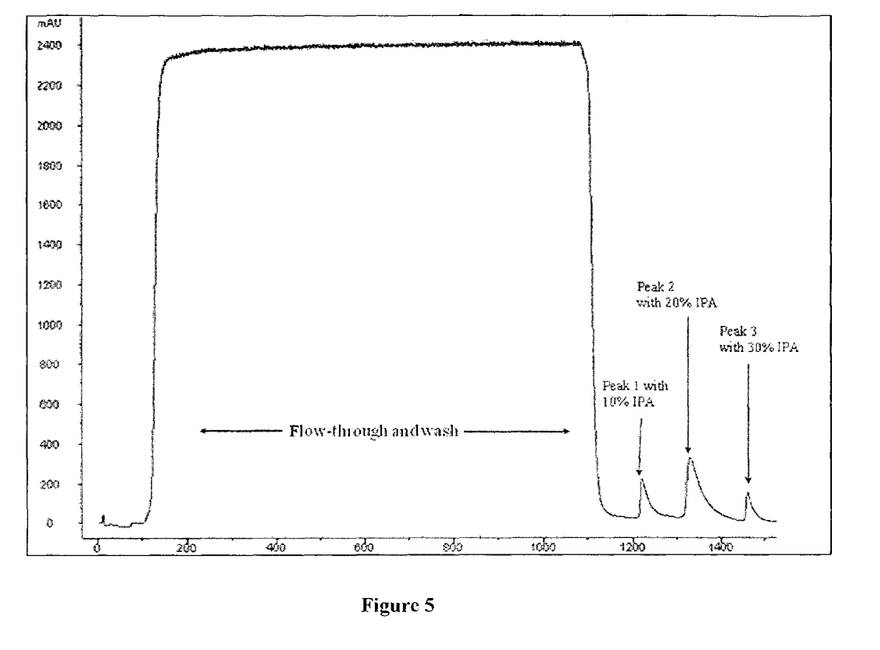
FIG. 5 illustrates a chromatogram of TNK-tPA purification from crude harvest by hydrophobic interaction column chromatography. Peak 1—with 10% isopropyl alcohol; Peak 2—with 20% isopropyl alcohol and Peak 3—with 30% isopropyl alcohol.

The cultured supernatant containing TNK-tPA protein, as described in example 1, was loaded on to a butyl sepharose 6 FF column. The column was equilibrated with 20 mM Tris-Cl buffer of pH 7.0 containing 750 mM NaCl. After loading, the column was washed with 10% isopropyl alcohol in the equilibration buffer. Majority of the impurities present in the crude mixture was found to wash-out of the column with 10% isopropyl alcohol. Elution of the desired tPA protein was eluted out of the column with buffer containing 20% isopropyl alcohol. Column was further washed with buffer containing 30% isopropyl alcohol to remove the strongly bound tPA protein along with other impurities. The chromatogram is illustrated in FIG. 5.

We claim:

1. A process for the purification of a tissue plasminogen activator protein comprising:
   a) loading a mixture of a tissue plasminogen activator protein with impurities on to a suitable column matrix;
   b) eluting the impurities from the column matrix with a suitable organic solvent at appropriate concentration;
   c) eluting the desired form of the tissue plasminogen activator protein from the column matrix with a suitable organic solvent at appropriate concentration;
   d) obtaining the tissue plasminogen activator protein in its desired form; and
   e) optionally, an ion exchange column step is used before or after using the suitable column matrix;
   wherein the suitable organic solvent is ethanol, methanol, or isopropyl alcohol, and
   wherein the suitable column matrix is hydrophobic interaction chromatography.

2. The process of claim 1, wherein the tissue plasminogen activator protein is selected from TNK-tPA, r-tPA, r-PA, and n-PA.

3. The process of claim 2, wherein the desired form of the tissue plasminogen activator protein comprises predominantly the single-chain form of tPA.

4. The process of claim 3, wherein the desired form of the tissue plasminogen activator protein comprises predominantly at least 55% single-chain form of tPA.

5. The process of claim 3, wherein the desired form of the tissue plasminogen activator protein comprises predominantly 60%-80% single-chain form of tPA.

6. The process of claim 1, wherein the tissue plasminogen activator protein comprises a mixture of single chain and double chain.

7. The process of claim 6, wherein the mixture comprises at least 60% single chain.

8. The process of claim 6, wherein the mixture comprises at least 60%-80% single chain.

9. The process of claim 1, wherein the impurities comprise predominantly double chain.

10. The process of claim 1, wherein the appropriate concentration used in step (b) is less than 15% of suitable organic solvent.

11. The process of claim 1, wherein the appropriate concentration used in step (b) is 5-14% of suitable organic solvent.

12. The process of claim 1, wherein the appropriate concentration used in step (c) is 16-30% of suitable organic solvent.

13. The process of claim 1, wherein the suitable organic solvent is isopropyl alcohol.

14. The process of claim 13, wherein the isopropyl alcohol is used in the range of 5% to 30%.

15. The process for the purification of the tissue plasminogen activator protein of claim 1 comprising:
   a) loading the mixture of the tissue plasminogen activator protein with impurities on to a hydrophobic interaction column matrix;
   b) washing of the hydrophobic interaction column matrix with less than 15% isopropyl alcohol to elute the impurities comprising mainly the double-chain form of tPA;
   c) eluting the tissue plasminogen activator protein in the desired form comprising predominantly the single-chain form in the presence of 15% to 30% of isopropyl alcohol through the hydrophobic column matrix;
   d) obtaining the tissue plasminogen activator protein in its desired form; and
   e) optionally, subjecting the tissue plasminogen activator protein in its desired form to an ion exchange column chromatography.

16. The process of claim 15, wherein the concentration of the isopropyl alcohol in step (b) is 5% to 14%.

17. The process of claim 15, wherein the concentration of the isopropyl alcohol in step (c) is 18% to 30%.

18. The process for the purification of the tissue plasminogen activator protein of claim 15 comprising:
   (a) loading the mixture of the tissue plasminogen activator protein with impurities on to a hydrophobic interaction column matrix;
   (b) washing of the hydrophobic interaction column matrix with less than 15% isopropyl alcohol to elute the impurities comprising mainly the double-chain form of tPA;
   (c) eluting the tissue plasminogen activator protein by isopropyl alcohol in a concentration range of 18% to 30% from the hydrophobic interaction column matrix;
   (d) obtaining the tissue plasminogen activator protein in its desired form; and
   (e) subjecting the tissue plasminogen activator protein to at least one additional matrix selected from the group consisting of ion exchange chromatography, hydroxyapatite chromatography, affinity chromatography and hydrophobic interaction chromatography.

19. The process of claim 1, wherein the tissue plasminogen activator protein is TNK-tPA.

20. The process of claim 1, wherein the appropriate concentration used in step (b) is 12.5% of suitable organic solvent.

21. The process of claim 1, wherein the appropriate concentration used in step (c) is 20% of suitable organic solvent.

22. The process of claim 15, wherein the concentration of isopropyl alcohol in step (b) is 10%.

23. The process of claim 15, wherein the concentration of isopropyl alcohol in step (b) is 12.5%.

24. The process of claim 15, wherein the concentration of isopropyl alcohol in step (c) is 20%.

25. The process of claim 18, wherein the concentration of isopropyl alcohol in step (c) is 20%.

\* \* \* \* \*